United States Patent [19]

Nishimura et al.

[11] Patent Number: 5,356,961
[45] Date of Patent: Oct. 18, 1994

[54] AQUEOUS EPOXY RESIN COMPOSITION

[75] Inventors: Toshiaki Nishimura; Kiichiro Seki; Yasushi Ohnuma, all of Hiratsuka, Japan

[73] Assignee: Mitsubishi Gas Chemical Company, Inc., Tokyo, Japan

[21] Appl. No.: 961,375

[22] Filed: Oct. 15, 1992

[30] Foreign Application Priority Data

Dec. 26, 1991 [JP] Japan .................. 3-345191

[51] Int. Cl.$^5$ .......................... C08K 3/20; C08L 63/02
[52] U.S. Cl. ........................... 523/414; 523/420
[58] Field of Search ................... 523/420, 414

[56] References Cited

U.S. PATENT DOCUMENTS 4,605,765  8/1986  Miyamoto et al. .................. 528/123

FOREIGN PATENT DOCUMENTS 095347   11/1983  European Pat. Off. .
0387948   5/1965  Switzerland .
2011421   7/1979  United Kingdom .

OTHER PUBLICATIONS

Lee & Neville, Handbook of Epoxy Resins (1967) pp. 10-5 and 24-29.

*Primary Examiner*—Melvyn I. Marquis
*Assistant Examiner*—D. Aylward
*Attorney, Agent, or Firm*—Frishauf, Holtz, Goodman & Woodward

[57] ABSTRACT

There is disclosed an aqueous epoxy resin composition which comprises an epoxy resin; an amidoamine obtained by the reaction of a carboxylic acid with a polyamine compound represented by the general formula (I)

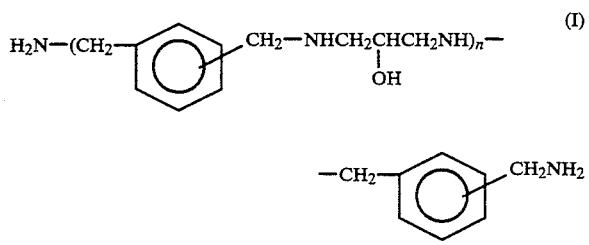

wherein n is an integer of 0 or 1 or greater indicating the number of the repeating units which compound is obtained by the reaction of epichlorohydrin with xylylenediamine, especially m-xylenediamine; and water. The above-mentioned epoxy resin composition can be utilized in a wide variety of industrial applications such as a coating material used for the purpose of anticorrosion or decoration, an adhesive for civil and building work or the like.

13 Claims, No Drawings

AQUEOUS EPOXY RESIN COMPOSITION

BACKGROUND OF THE INVENTION

1. Field of the Invention

The present invention relates to an aqueous epoxy resin composition containing water as the medium. More particularly, it pertains to an aqueous epoxy resin composition that can be utilized in a wide variety of industrial applications such as a coating material used for the purpose of anticorrosion or decoration, an adhesive for civil and building work or the like.

2. Description of Related Art

An epoxy resin is widely utilized in a variety of industrial fields by virtue of a number of excellent characteristics in comparison with the other types of resins in terms of adhesivity to various substrates, heat resistance, chemical resistance, electrical properties and mechanical properties. In recent years it has been particularly active in the field of coating materials.

In general, the types of the epoxy resin compositions that are employed in the field of coating material or adhesive are roughly classified into liquid type without the use of a solvent (solventless type), liquid type by the use of an organic solvent as the principal medium, liquid type by the use of water as the medium and solid type (powder).

Among the aforementioned types, the solventless type epoxy resin composition is used as the composition in which an epoxy resin in the form of liquid at ordinary temperature is lowered in its viscosity by the use of a low-viscosity curing agent and a high boiling diluent. However, it is inevitable that, in the course of producing a low-viscosity curing agent, a large amount of free amines and phenols that are harmful to human beings have to be used, and even in the case of a diluent that is relatively less harmful to human beings, the use of such diluent deteriorates the performance of a curing agent.

The liquid type epoxy resin composition using an organic solvent as the principal medium is used generally by dissolving a high molecular epoxy resin in the form of solid at ordinary temperature by the use of a low-viscosity solvent such as xylene, toluene, cellosolve, ethanol or n-butanol and permits a wide selective range of curing agents. Accordingly, the above-mentioned composition not only affords a high-performance cured product but also permits the arbitrary regulation of the viscosity of the composition, thereby finding a number of applications for the above-mentioned purposes. Nevertheless, the composition suffers the disadvantage including harmfulness to the workers handling such an organic solvent, environmental pollution and possibility of such hazard as fire or explosion.

On the other hand, the solid-type epoxy composition is a combined product of a solid epoxy resin with a solid curing agent. The purpose of use thereof is principally a coating material but is limited with regard to its workability. On the contrary, the aqueous epoxy resin composition is obtained by dispersing or dissolving an epoxy resin and a curing agent in water and forms a composition excellent in workability free from the aforesaid drawback which is inherent in the other types of compositions except for the performance of the cured product therefrom.

It is the present situation, however, that an aqueous epoxy resin composition having satisfactory performance has not yet been developed by reason of a large amount of a surfactant required, unavailability of a proper curing agent and the like. There have certainly been partly put into practical use or suggested aqueous epoxy resin compositions using as a curing agent, an adduct of diethylene triamine to an epoxy compound or an amidoamine obtained by reacting an aliphatic amine such as ethylenetriamine with an aliphatic carboxylic acid. Nevertheless, any of the above-mentioned curing agents is far from overcoming the aforestated disadvantages.

As a result of intensive research and investigations made by the present inventors on the above-described subject, it has been discovered by them that the problem can be solved by dispersing in water a curing agent comprising an epoxy resin and a specific amidoamine. The present invention has been accomplished on the basis of the foregoing finding.

SUMMARY OF THE INVENTION

It is an object of the present invention to provide an aqueous epoxy resin composition well suited for use in a coating material or an adhesive, which composition is free from the problems including harmfulness to human beings, possibility of such hazard as fire or explosion or environmental pollution each originating from the use of an organic solvent.

It is another object of the present invention to provide an aqueous epoxy resin composition well suited for use in a coating material or an adhesive, which composition has a short curing time, a low viscosity and favorable workability.

It is still another object of the present invention to provide an aqueous epoxy resin composition well suited for use in a coating material or an adhesive, characterized by the excellent perforcemance of the cured product therefrom, especially adhesivity to a variety of substrates.

Other object of the present invention will become apparent from the detailed description to follow taken in conjunction with the appended claims.

For the above-mentioned objects, the present invention provides an aqueous epoxy resin composition which comprises an epoxy resin; an amidoamine obtained by the reaction of a carboxylic acid with a polyamine compound represented by the general formula (I)

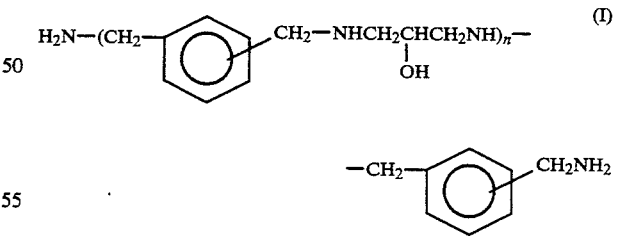

wherein n is an integer of 0 or 1 or greater indicating the number of the repeating units which compound is obtained by the reaction of epichlorohydrin with xylylenediamine; and water.

DESCRIPTION OF PREFERRED EMBODIMENT

The epoxy resin to be employed in the present invention is exemplified by so called btsphenol A-type epoxy resin obtained by the reaction of bisphenol A with epichlorohydrin; so called bisphenol F-type epoxy resin obtained by the reaction of bisphenol F with epichlorohydrin; and so called bisphenol AD-type epoxy resin obtained by the reaction of bisphenol AD with epichlorohydrin and the like, of which is preferable an epoxy resin in the form of liquid at 30° C.

The amidoamine which functions as the curing agent in the composition according to the present invention is obtained by reacting epichlorohydrin with stoichiometrically excess xylylenediamine in the presence of an alkali to produce a polyamine compound represented by the above-mentioned general formula (I) and subsequently reacting the resultant polyamine compound with a carboxylic acid. As mentioned before, the polyamine compound is represented by the general formula (I) and, in the case where xylylenediamine is m-xylylenediamine, it becomes a preferred polyamine represented by the general formula (II)

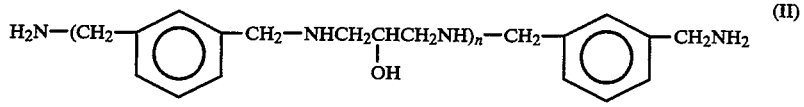 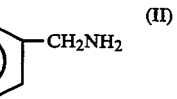

Here, the preferred xylylenediamine is m-xylylenediamine, but there is usable a xylylenediamine containing p-xylylenediamine to some extent.

The amidoamine to be employed in the present invention is obtained by the reaction of the aforestated polyamine compound with a carboxylic acid as mentioned before and may be diluted with water at the time of use, if necessary.

Examples of carboxylic acid to be used include oxyalic acid, malonic acid, succinic acid, glutaric acid, adipic acid, a dimer acid, acetic acid, propionic acid, burytic acid, palmitic acid, stearic acid, oleic acid, linolic acid, linoleic acid and a fatty acid from tall oil, of which are preferable a dimer acid and a fatty acid from tall oil, each of them being usable alone or as the mixture with the other.

The epoxy resin and amidoamine to be used in the present invention may allow a small amount of a surfactant, an organic solvent that is generally used in a coating material or the like to coexist therewith as required for the purpose of improving dispersibility.

To the composition of the present invention, there may be optionally added a publicly known pigment such as calcium carbonate and talc, a filler, a levelling agent, an antiform.

The proportions of the epoxy resin, amidoamine and water in the composition of the present invention are not specifically limited but may be optionally selected according to the purpose of use. In general, however, the amidoamine is incorporated therein in an amount of 40 to 170, preferably 80 to 120 parts by weight based on 100 parts by weight of the epoxy resin having an epoxy equivalent of 160 to 200; and 15 to 100, preferably 25 to 60 parts by weight based on the same parts of the epoxy resin having an epoxy equivalent of 400 to 600, and water in an amount of 10 to 90, preferably 30 to 60 parts by weight based on the same parts of the epoxy resin.

The aqueous epoxy resin composition according to the present invention has a high curing rate (rapid rising in pencil hardness) and provides a cured coating excellent in external appearance and adhesivity.

Therefore, the aqueous epoxy resin composition of the present invention can be utilized in a wide variety of industrial applications such as a coating material used for the purpose of anticorrosion or decoration, an adhesive for civil and building wark or the like.

In the following, the present invention will be described in more detail with reference to the non-limitative examples and a comparative example, in which the evaluation and indication for the cured coating were made in accordance with the following.

(1) External appearance

The following symbols were used to evaluate the external appearance of cured coating such as laster, transparency and smoothness Ex:Excellent G:Good F:Fair
P:Poor (2) Pencil hardness and adhesivity to steel plate The tests of pencil hardness, Erichsen and cross-cut test were carried out in accordance with JIS K 5400.

Example 1
(1) Synthesis of polyamine

In a vessel reactor equipped with an agitator, a thermometer, a tube for feeding nitrogen, a dropping funnel and a condenser were fed 272 g of m-xylylenediamine and 81.6 g of 50% aqueous solution of sodium hydroxide and 92.5 g of epichlorohydirn was added dropwise to the mixture at 70° C. under stirring in a nitrogen atmosphere over a period of one hour. After the completion of dropwise addition, reaction was carried out for 3 hours at a reaction temperature raised as high as 110° C. Thereafter the reaction product was cooled to 50° C. and filtered to remove sodium chloride and sodium carbonate, and the filtrate was distilled at 80° to 100° C. under a reduced pressure of 100 mmHg to distil away water. After the above distillation, the sodium chloride deposited in the bottoms of the reactor was filtered away to obtain the objective polyamine compound.

(2) Synthesis of amidoamine

In the above-mentioned vessel reactor were fed 328 g of the polyamine thus obtained and 116 g of a dimer acid. The resultant mixture was heated to 180° C. in a nitrogen atmosphere and reacted for one hour while the condensed water was distilled away. Then the reactant was heated to 200° C. to proceed with reaction for 2 hours, followed by further reaction for 2 hours at a temperature raised to 230° C. to finalize the reaction. Thereafter the reaction product was allowed to cool to 100° C. and diluted with water so as to attain a solid content of 60% by weight to produce an aqueous amidoamine composition having an active hydrogen equivalent of 140.

(3) Preparation of aqueous epoxy resin composition

The aqueous amidoamine composition thus obtained in an amount of 40 g was added to 100 g of the aqueous epoxy resin emulsion having an epoxy equivalent of 340 and a solid content of 70% by weight (produced by Asahi Denka Kogyo K. K. under the tradename of Adeka resin EPE-0410) and the mixture was stirred in a dissolver for 5 minutes to obtain an aqueous epoxy resin composition.

The aqueous epoxy resin composition thus obtained was coated over the surface of a cold rolled carbon steel sheet with a size of 70×150×0.8 mm which had been treated with #240 sand paper by the use of 200 μm doctor blade and cured for 7 days under the conditions of 23° C. and 50% relative humidity (RH). Table 1 collectively gives the compounding ratio of the composition used in the test and the result of evaluation for the coating thus prepared.

Example 2

The procedure in Example 1 (2) was repeated to obtain an aqueous amidoamine composition having an active hydrogen equivalent of 140 and a solid content of 60% by weight except that 87 g of the dimer acid and 29 g of a fatty acid from tall oil were used in place of 116 g of the dimer acid.

Following the above procedure, an aqueous epoxy resin composition was obtained in the same manner as in Example 1 (3). The composition thus obtained was coated over the surface of a cold rolled carbon steel sheet to form coating on the sheet in the same manner as in Example 1 and the coating was evaluated by the same method as in Example 1. Table 1 collectivly gives the compounding ratio of the composition used in the test and the result of evaluation for the resultant coating.

Comparative Example 1

In the reactor same that used in Example 1 were fed 146 g of triethylenetetramine, 174 g of a dimer acid and 116 g of a fatty acid from tall oil reaction was carried out in the same manner as in Example 1 (2) to obtain an aqueous amidomaine composition having an active hydrogen equivalent of 176 and a solid content of 60% by weight.

A part of the resultant aqueous amidoamine composition in an amount of 52 g was added to 100 g of the aqueous epoxy resin emulsion (Adeka resin EPE-0410) and an aqueous epoxy resin composition was obtained by the same procedure as in Example 1 (2).

The resultant composition was coated over the surface of a cold rolled carbon steel sheet to form coating on the sheet in the same manner as in Example 1 and the coating was evaluated by the same method as in Example 1. Table 1 collectively gives the compounding ratio of the composition used in the test and the result of evaluation for the resultant coating.

TABLE 1

|  | Example 1 | Example 2 | Comparative Example 1 |
| --- | --- | --- | --- |
| Compounding ratio (part by weight) |  |  |  |
| (A) Epoxy resin*1 | 100 | 100 | 100 |
| (B) Curing agent*2 | 40 | 40 | 50 |
| Solid content of A + B (%) | 67 | 67 | 67 |
| Evaluation results of coating |  |  |  |
| Film thickness (μm) | 51 | 48 | 52 |
| External appearance (after a day from coating) |  |  |  |
| Luster | Ex | Ex | P |
| Transparency | G | G | F |
| Smoothness | Ex | G | P |
| Pencil hardness test |  |  |  |
| After a day from coating | H | H | B |
| After 7 days from coating | H | 2H | B |
| Adhesivity to carbon steel sheet |  |  |  |
| Erichsen test (mm) | 8.5 | 9.0 | 6.5 |
| Cross-cut test | 100/100 | 100/100 | 72/100 |

*1Solid content of 70% by weight
*2Solid content of 60% by weight

What is claimed is:

1. An aqueous epoxy resin composition which consists essentially of an (i) epoxy resin; (ii) an amidoamine obtained by the reaction of a carboxylic acid with a polyamine compound of the formula (I)

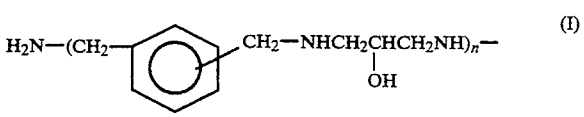

wherein n is an integer of 1 or greater indicating the number of the repeating units, said polyamine compound being obtained by the reaction of epichlorohydrin with xylylenediamine; and (iii) water.

2. The composition according to claim 1 wherein the xylylenediamine is m-xylylenediamine and the polyamine compound is of the formula (II)

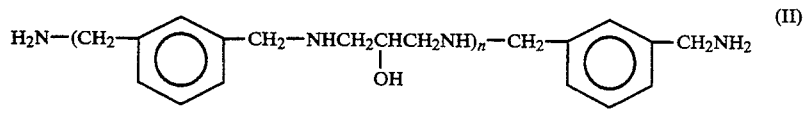

wherein n is an integer of 1 or greater indicating the number of the repeating units.

3. The composition according to claim 1 wherein the epoxy resin is obtained by a reaction of a bisphenol A with epichlorohydrin.

4. The composition according to claim 1 wherein the epoxy resin is in the form of a liquid at 30° C.

5. The composition according to claim 1 wherein n is an integer from 1 to 12 indicating the number of the repeating units.

6. The composition according to claim 1 wherein the carboxylic acid is at least one acid selected from the group consisting of a dimer acid and a fatty acid from tall oil.

7. The composition according to claim 1 wherein the amidoamine is contained in an amount of 40 to 170 parts by weight and water is contained in an amount of 10 to 90 parts by weight each based on 100 parts by weight of the epoxy resin having an epoxy equivalent of 160 to 200.

8. The composition according to claim 4 wherein the amidoamine is contained in an amount of 80 to 120 parts by weight and water is contained in an amount of 30 to 60 parts by weight, each based on 100 parts by weight of the epoxy resin having an epoxy equivalent of 160 to 200.

9. The composition according to claim 8 wherein the epoxy resin is obtained by reacting bisphenol A with epichlorohydrin.

10. The composition according to claim 9 wherein the amidoamine is obtained by reacting m-xylylenediamine with a carboxylic acid selected from the group consisting of oxyalic acid, malonic acid, succinic acid, glutaric acid, adipic acid, acetic acid, propionic acid, butyric acid, palmitic acid, stearic acid, oleic acid, linolic acid, linoleic acid, a dimer acid and a fatty acid from tall oil.

11. The composition according to claim 2, wherein the amidoamine is contained in an amount of 25 to 60 parts by weight and water is contained in an amount of 30 to 60 parts by weight, each based on 100 parts by weight of the epoxy resin having an epoxy equivalent of 400 to 500; the epoxy resin is obtained by a reaction of a bisphenol A with epichlorohydrin; and the epoxy resin is a liquid at 30° C.

12. The composition according to claim 11, wherein the amidoamine is contained in an amount of 15 to 100 parts by weight and water is contained in an amount of 10 to 90 parts by weight, each based on 100 parts by weight of the epoxy resin having an epoxy equivalent of 400 to 600.

13. The composition according to claim 12, wherein the amidoamine is obtained by reacting m-xylylenediamine with a carboxylic acid selected from the group consisting of oxyalic acid, malonic acid, succinic acid, glutaric acid, adipic acid, acetic acid, propionic acid, butyric acid, palmitic acid, stearic acid, oleic acid, linolic acid, linoleic acid, a dimer acid and a fatty acid from tall oil.

* * * * *